US 6,587,709 B2

(12) United States Patent
Solf et al.

(10) Patent No.: US 6,587,709 B2
(45) Date of Patent: Jul. 1, 2003

(54) METHOD OF AND IMAGING ULTRASOUND SYSTEM FOR DETERMINING THE POSITION OF A CATHETER

(75) Inventors: Torsten Solf, Aachen (DE); Kai Eck, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/109,239

(22) Filed: Mar. 28, 2002

(65) Prior Publication Data

US 2003/0060700 A1 Mar. 27, 2003

(30) Foreign Application Priority Data

Mar. 28, 2001 (DE) ......................................... 101 15 341

(51) Int. Cl.[7] ................................................ A61B 5/05
(52) U.S. Cl. ....................................... 600/424; 128/916
(58) Field of Search ............................. 600/424, 461, 600/437, 407, 447; 128/916

(56) References Cited

U.S. PATENT DOCUMENTS

| 4,706,681 A | 11/1987 | Breyer et al. ............... 128/642 |
| 5,797,849 A | * 8/1998 | Vesely et al. ............... 600/461 |
| 6,038,468 A | * 3/2000 | Rex ............................. 600/424 |
| 6,298,261 B1 | * 10/2001 | Rex ............................. 600/424 |

FOREIGN PATENT DOCUMENTS

| WO | WO 9625881 | 8/1996 | ............ A61B/8/08 |
| WO | WO 0007501 | 2/2000 | ............ A61B/8/12 |

* cited by examiner

Primary Examiner—Marvin M. Lateef
Assistant Examiner—Ruby Jain
(74) Attorney, Agent, or Firm—John Vodopia

(57) ABSTRACT

An imaging ultrasound system is provided with an ultrasound transducer and an image processing unit for the acquisition of a three-dimensional ultrasound image of the body of a patient, and a catheter for carrying out a therapeutic or diagnostic intervention in the body of the patient. The catheter accommodates, in addition to the customary instruments necessary to carry out its task, three ultrasound receivers that are mounted at a distance from one another on the tip of the catheter and are capable of detecting the arrival of scan signals of the ultrasound transducer. The distance between the ultrasound transducer and the receivers can be calculated from the transit time of the scan signals. The receivers can thus be localized in space. Localization enables notably the selection of, for example, the plane from the three-dimensional ultrasound data that contains all three receivers of the catheter. The tip of the catheter can thus be automatically tracked and displayed on a monitor at all times without manual displacement of the ultrasound transducer being necessary.

11 Claims, 2 Drawing Sheets

METHOD OF AND IMAGING ULTRASOUND SYSTEM FOR DETERMINING THE POSITION OF A CATHETER

The invention relates to a method of determining the position of a catheter in an ultrasound image acquired by means of an ultrasound transducer. The invention also relates to an imaging ultrasound system that is intended for imaging a region of a body and is suitable for carrying out such a method.

The determination of the position, or localization, of a catheter introduced into the vascular system of a patient is performed preferably by means of X-ray fluoroscopy in conformity with the present state of the art. This is applicable notably to examinations and therapeutic interventions in the cardiovascular field. Even though X-ray fluoroscopy is comparatively simple in respect of application, it has the drawback that the patient and the medical staff are exposed to radiation.

In order to avoid such a radiation load it is known to track and guide a catheter by way of an imaging ultrasound system. Systems of this kind offer the additional advantage of soft tissue contrast. It is particularly desirable to use 3D ultrasound scanners that acquire image information in real time from a three-dimensional body volume by means of ultrasound transducer units that are arranged in a flat two-dimensional array (2D). In achieving an appropriate and suitably understandable representation of the three-dimensional information, however, a further problem is encountered. When a two-dimensional image plane is selected from the scanned volume so as to be displayed, it usually does not contain the catheter which, therefore, cannot be guided by way of such an image section. Movements of the body that are due to, for example, respiration or cardiac action complicate matters further. The ultrasound source used, therefore, usually has to be displaced and re-oriented by hand and continuously so as to track the position of interest of the catheter.

U.S. Pat. No. 4,706,681 discloses a method of determining the position of the tip of a stimulation electrode that is arranged in the heart; according to this method an ultrasound receiver is integrated in said tip. This receiver generates an electric signal when it is struck by the fan-shaped two-dimensional scan beam of a 1D ultrasound transducer. This signal is fed out via the electrode wire and can be detected by an evaluation unit. The occurrence of this signal thus provides an indication that the tip of the electrode is situated exactly in the radiation range of the ultrasound transducer. This makes it possible to distinguish the tip of the electrode from an arbitrary section through the electrode wire in the ultrasound image. However, the position of the electrode cannot be determined beyond the image information of the ultrasound transducer.

WO 96/25881 discloses a method of tracking the position of an instrument inside the body of a patient; according to this method the region of operation of the instrument is monitored and displayed by means of an imaging ultrasound system, the position of the instrument being determined at the same time by way of a magnetic positioning system. In the case of a rigid instrument the position of its end that is situated outside the body can thus be determined and the position of the tip that is situated inside the body can be deduced therefrom. The information of the positioning system and of the ultrasound system is then combined in the reproduction of the region of operation in an image processing system.

Furthermore, U.S. Pat. No. 5,954,649 and WO 00/07501 disclose methods in which one or more reference catheters with ultrasound transmitters are introduced into the body and a catheter that is to be monitored and is provided with at least one ultrasound receiver is positioned in the vicinity of the region of operation. This arrangement enables determination of the position of the catheter relative to the reference catheters by measurement of the transit time of ultrasound signals. However, it is a drawback that additional reference catheters must be used and that the position is determined only with respect to the reference catheters whose location itself is not known exactly.

Considering the foregoing it was an object of the present invention to provide a method of and a system for the imaging of a catheter within the body of a patient that are less of a burden to the patient and at the same time provide more information for the user.

This object is achieved by means of a method as disclosed in the characterizing part of claim 1 and by means of an imaging system as disclosed in the characterizing part of claim 8. Further advantageous embodiments are disclosed in the dependent claims.

The method serves to determine the position of a catheter in an ultrasound image acquired by means of an ultrasound transducer; in this method the ultrasound transducer is provided in known manner with at least one transmission element for the transmission of ultrasound scan signals and at least one receiving element for the reception of echoes of the scan signals that emanate from the body. The transmission and receiving element (elements) may also be one and the same element. Furthermore, in conformity with the method the catheter is provided with at least one ultrasound receiver that detects the reception of ultrasound scan signals that were emitted by the ultrasound transducer. The transit time of the ultrasound scan signals from the transmission element of the ultrasound transducer to the receiver in the catheter is then measured and the distance between the ultrasound transducer or the receiving element and the receiver on the catheter is determined from the transit time thus measured.

The described method offers the advantage that it enables more accurate determination of the position of the catheter relative to the ultrasound transducer that is usually situated outside the body, because the respective distance between these two elements is determined in conformity with this method. The information thus obtained can then be used for more exact localization of the catheter of interest in an ultrasound image.

Preferably, the ultrasound transducer is configured in such a manner that it acquires a three-dimensional ultrasound image. Such a transducer includes a plurality of transmission units, so that the distance can be determined between the ultrasound receiver or the ultrasound receivers on the catheter and each of the transmission units. This enables determination of the exact position in space of each ultrasound receiver on the catheter.

When an ultrasound transducer that acquires a three-dimensional image is used, the proposed method enables, on the basis of the position of the ultrasound receiver on the catheter that can thus be detected, a plane to be selected for display from the three-dimensional ultrasound image, that is, in dependence on the position of said ultrasound receiver. This plane may notably be a plane that contains the ultrasound receiver and hence also the catheter. Consequently, it is no longer necessary to displace the ultrasound transducer or the plane reproduced in the three-dimensional ultrasound image in conformity with the catheter by hand; this plane can now be found automatically by means of the position of the ultrasound receiver on the catheter.

The catheter preferably includes at least three ultrasound receivers so that the position in space of three different points of the catheter can be determined. These three points then define a plane wherethrough the catheter extends. When this plane is selected for display from a three-dimensional ultrasound image, it is ensured that it will contain the catheter for a prolonged period of time. For the exceptional case where all ultrasound receivers on the catheter are oriented along one line and hence do not define an unambiguous plane, an arbitrary one of said planes can be selected for display; all three of said planes then contain an ultrasound receiver.

For the display of the acquired ultrasound image, for example, on a monitor, the position of the receiver or the receivers on the catheter that is known from the transit time measurements is preferably highlighted. This offers the user information as to where the receivers, whose position is known exactly, are situated.

In conformity with a further version of the method, a sub-region to be displayed is determined from the overall ultrasound scan volume by means of the position determined for the ultrasound receivers of the catheter. The subsequent ultrasound display can then be concentrated on this sub-region. The determination of the position of the catheter thus enables a "region of interest" (ROI) to be determined from the total scanned body volume. Limiting the image acquisition to this ROI then offers a substantial saving of time that can be used for higher image acquisition rates, for noise reduction, for multifocus etc.

Using the catheter whose position is determined via the ultrasound receiver arranged thereon, preferably further measuring data is also acquired; such further data can be associated with the position of the ultrasound receiver then determined. Such measuring data may notably be electrophysiological data, for example, stimulation lead potentials at the heart.

The invention also relates to an imaging ultrasound system for the imaging of a part of a body, which system includes the following elements:

an ultrasound transducer that is provided with at least one transmission unit for transmitting ultrasound scan signals and with at least one receiving unit for receiving echoes of the scan signals;

an image processing unit that is coupled to the ultrasound transducer and is arranged to calculate an image of the part of the body from the measuring signals provided by the ultrasound transducer;

at least one catheter that is provided with at least one ultrasound receiver that is coupled to the image processing unit.

The image processing unit is arranged to determine the distance between the transmission unit and the receiver (receivers) from the measured transit time of the scan signals from the transmission unit of the ultrasound transducer to the receiver or to the receivers of the catheter. Such an imaging system thus enables more exact determination of the position of the catheter.

The imaging system is notably arranged or configured in such a manner that it is suitable for carrying out a method of the kind set forth.

The ultrasound transducer preferably includes a plurality of ultrasound transmission units and ultrasound receiving units and is arranged to acquire a three-dimensional ultrasound image in conjunction with the image processing unit. When such an ultrasound transducer is provided with a plurality of transmission units, the distance between each transmission unit and each receiver on the catheter can be determined. The exact position of the catheter receiver in the scanned 3D volume can be determined from the known pulse generation timing of the imaging system and the transit time measurements of the catheter receivers.

The catheter preferably also includes at least three ultrasound receivers, so that the position of three different points of the catheter can be determined. These three points can then be used to define a plane to be imaged from a three-dimensional ultrasound image, said plane containing at least a section of the catheter.

Preferably the catheter also includes further medical instruments, such as notably electrodes, for the acquisition of electrophysiological data. This means that the catheter may be a known therapeutic or diagnostic instrument which, because of the additional provision of ultrasound receivers, is particularly suitable for use in combination with a method that employs ultrasound monitoring.

The invention will be described in detail hereinafter, by way of example, with reference to the Figures. Therein:

Figure 1:
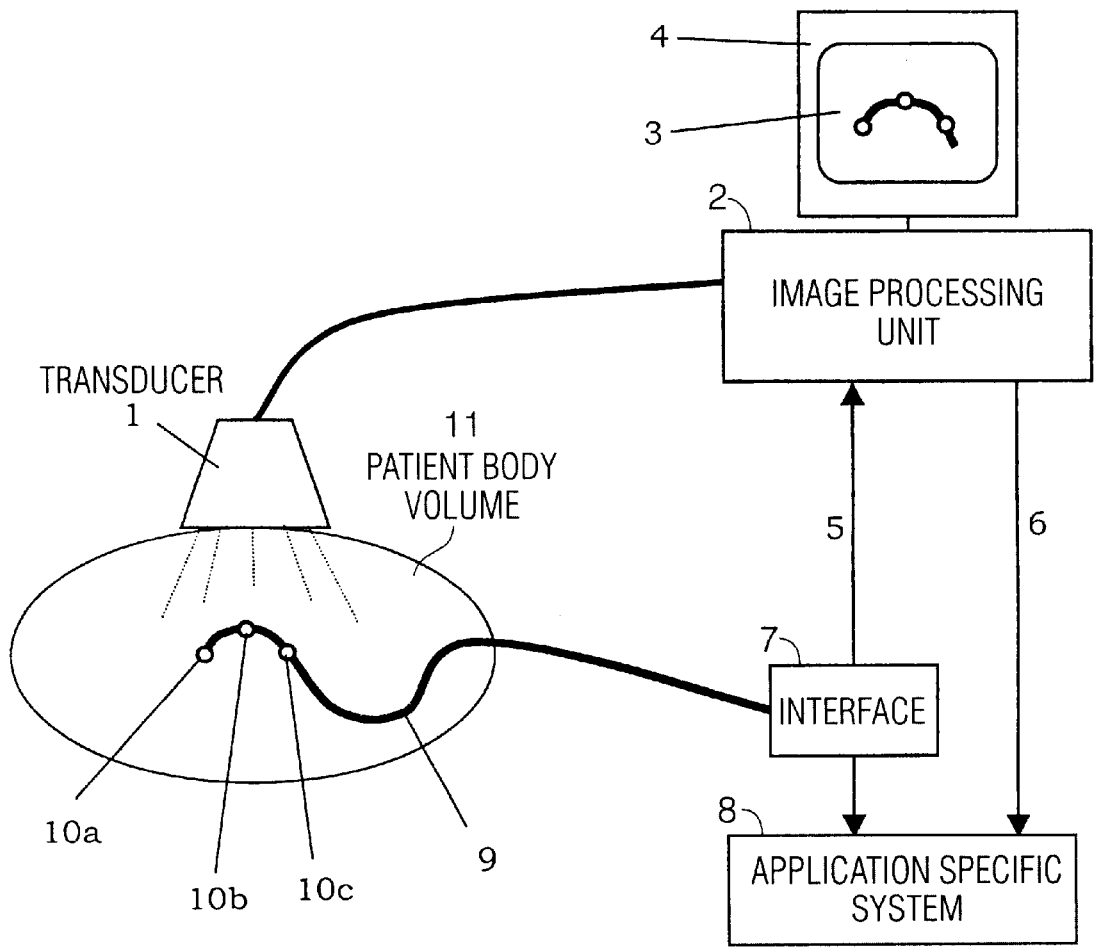
FIG. 1 shows diagrammatically the components of an imaging system for determining the position of a catheter.

The imaging system that is shown in FIG. 1 consists essentially of a 2D ultrasound transducer 1 that is connected to a 3D image processing unit 2, as well as of a (disposable) catheter 9 that is provided, near its tip, with three ultrasound receivers 10a, 10b and 10c that are also connected to the image processing unit 2 via an interface 7.

The ultrasound transducer 1 and the image processing unit 2 serve in known manner for the acquisition of a three-dimensional echo image of the body volume of a patient 11 that is present in the radiation range of the two-dimensionally distributed transmission units of the ultrasound transducer 1. From the volumetric ultrasound data thus obtained a plane can be selected so as to be displayed on a monitor 4 that is connected to the image processing unit 2. Simultaneous display of a plurality of planes or display of a three-dimensional image (for example, using 3D spectacles) is also possible.

The catheter 9 may in principle be any type of catheter that is customarily used for treatment or diagnosis. The catheter may be intended especially for carrying out operations such as PTCA (Percutaneous Transluminal Coronary Angioplasty), perfusion measurement, electrophysiological mapping, ablation, blood pressure measurements and so on. Furthermore, cardiac wall contact can also be suitably followed by means of the system in accordance with the invention.

For the monitoring and guiding of the catheter 9 it is desirable that its tip is reproduced permanently, if possible, on the monitor 4. Whereas in conventional systems such reproduction can be achieved only by continuous manual adjustment of the imaging plane, in the system in accordance with the invention this plane can be automatically recognized and selected for display on the display screen 4.

In order to enable the foregoing operation, three ultrasound receivers 10a, 10b and 10c are arranged at a distance from one another on the tip of the catheter 9. These receivers are capable of detecting the ultrasound pulses that are generated by the ultrasound system. The measured signals are then applied, via the interface 7 and a lead 5, to the image processing unit 2 which calculates in real time the position of each of the three receivers 10a, 10b, 10c from the measured transit times of the received pulses while the pulse sequence and geometry of the ultrasound transducer 1 are known. The three ultrasound receivers, and hence the tip of the catheter 9, can thus be localized relative to the ultrasound transducer that is situated outside the body. The image processing unit 2 can thus utilize the known positions of the ultrasound receivers 10a, 10b and 10c to select a suitable imaging plane 3 from the volumetric ultrasound data so as to display this plane on the monitor 4. Preferably, this is the plane that contains all three ultrasound receivers 10a, 10b and 10c. The positions of the receivers can additionally be highlighted in the image thus formed.

The automatic selection of the "correct" plane, that is, the plane containing the catheter 9, from the volumetric ultrasound data enables the ultrasound transducer 1 to remain stationary and oriented in the same way throughout the examination, so that readjustment by hand is not necessary.

Should the three ultrasound receivers 10a, 10b and 10c be situated along a straight line by way of exception, they will not define an unambiguous plane. In that case, for example, the plane that contains the three receivers and is oriented in a predetermined direction is selected.

The automatic determination of the position of the catheter 9, as enabled by the proposed system, also makes it possible to isolate a sub-region from the scanned volume so as to ignore edge regions that are not of interest in subsequent ultrasound images. The ultrasound method can thus be automatically concentrated on a Region Of Interest (ROI), so that the necessary exposure time can be reduced and hence a higher image rate can be achieved for the ultrasound system.

Using an output lead 6, the three-dimensional position information can also be applied from the image processing unit 2 to another, notably application-specific system 8. For example, an instrument that is additionally provided on the catheter 9 can be actuated when the ultrasound receivers 10a, 10b and 10c reach a given position.

The interface 7 is also connected to the application-specific system 8 via a lead 7 for the exchange of information. For example, electrophysiological signals that are measured by the catheter can be conducted via said lead 7.

Figure 2:
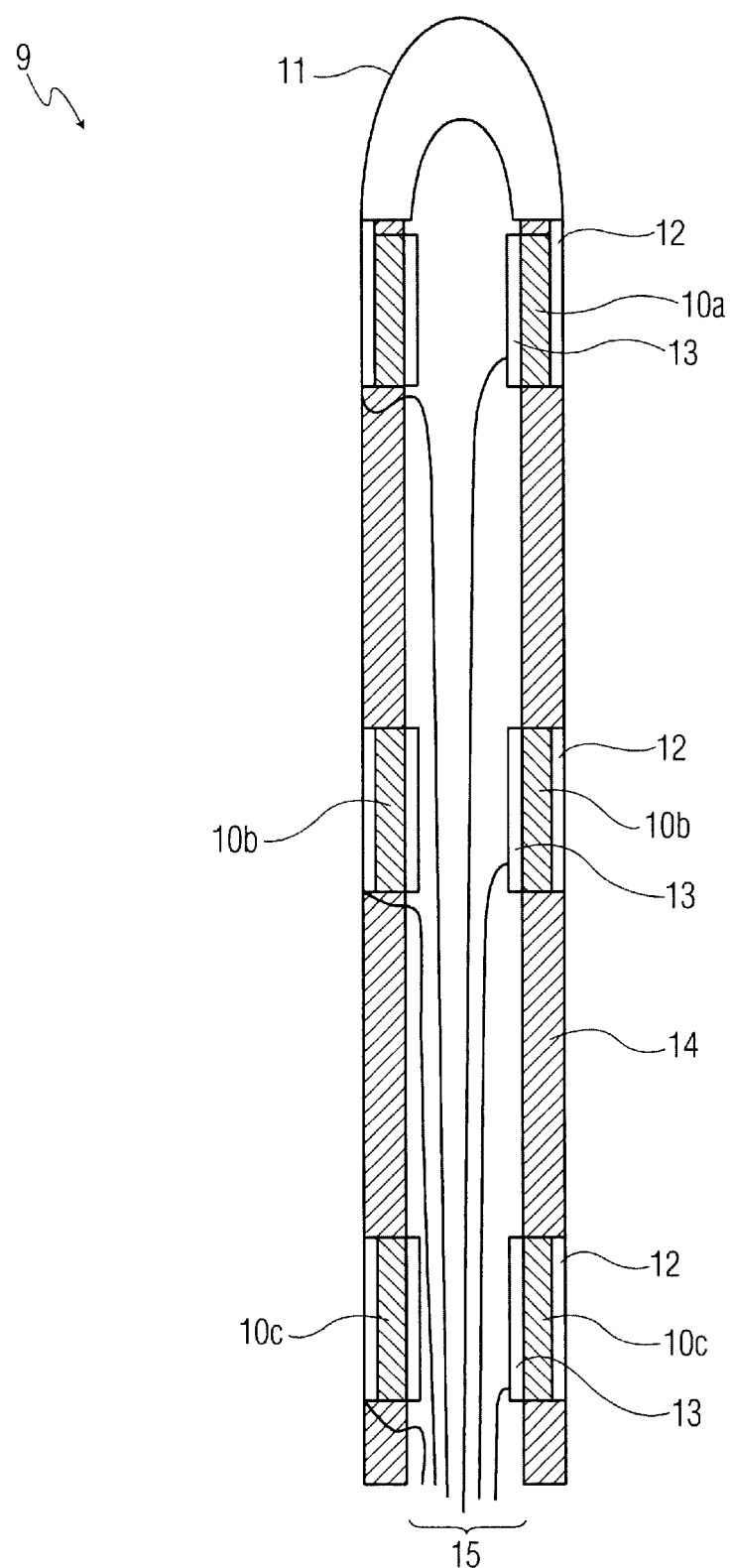
FIG. 2 shows the tip of the catheter used in the system that is shown in FIG. 1.

FIG. 2 is a more detailed representation of a feasible configuration of the distal end of the catheter 9. The catheter 9 has a rounded tip 11 that closes off a flexible catheter tube 15. Three ring electrodes 12 are provided at a distance from one another along the tube 15, said electrodes enabling the acquisition of electrophysiological data. Underneath the ring electrodes 12 there is provided a respective ring-shaped piezoelectric receiving element 10a, 10b and 10c. Such a piezoelectric element generates an electric signal when it is exposed to an ultrasound scanning pulse from the ultrasound transducer 1 (FIG. 1).

At its side that faces the lumen of the catheter 9 each ultrasound element is covered by a respective inner electrode 13. All electrodes 12, 13 are connected to leads that extend through the lumen of the catheter 9 and are fed as a bundle 15 to the interface 7 (FIG. 1).

The catheter shown is particularly suitable for the analysis of cardiac arrhythmia. The three-dimensional position information may then be useful for electrophysiological mapping, because the electrical activities of the heart can be superposed directly on geometrical information. This enables the formation of an anatomical map that represents the progression of the electrical excitation and identification of the cause of the arrhythmia.

What is claimed is:

1. A method of determining a position of a catheter in an ultrasound image acquired by means of an ultrasound transducer, comprising the steps of:

providing the catheter with at least one ultrasound receiver that detects a reception of ultrasound scanning signals transmitted by the ultrasound transducer, acquiring a three-dimensional ultrasound image, displaying the three-dimensional ultrasound image, determining a distance between the ultrasound transducer and the ultrasound receiver on the catheter from a measured transit time of the scanning signals, and calculating a position in space of the ultrasound receiver on the catheter.

2. A method as claimed in claim 1, wherein the step of calculating further includes calculating the position in space of the ultrasound receiver on the catheter from the measured transit time of the scan signals.

3. A method as claimed in claim 2, wherein the step of displaying the three-dimensional ultrasound image includes that at least one plane is selected from the three-dimensional ultrasound image in dependence on the position in space determined for the ultrasound receiver or the catheter.

4. A method as claimed in claim 3, wherein the step of displaying further includes that the at least one plane contains at least one of the ultrasound receivers selected from the three-dimensional ultrasound image for display, so that the position in space of the ultrasound receiver on the catheter in space can be tracked continuously.

5. A method as claimed in claim 1, wherein the step of displaying includes that the position in space of the ultrasound receiver on the catheter is highlighted in the ultrasound image.

6. A method as claimed in claim 1, wherein a sub-region of a scanning volume is determined on the basis of the position in space determined for the ultrasound receiver, with any subsequent ultrasound imaging being concentrated on said sub-region.

7. A method as claimed in claim 1, further including acquiring electrophysiological data by the catheter so as to be associated with the position in space determined for the ultrasound receiver.

8. An imaging ultrasound system for the imaging of a part of a body, which system includes:

an ultrasound transducer provided with at least one transmission unit for transmitting ultrasound scan signals and with at least one receiving unit for receiving echoes of the ultrasound scan signals;

an image processing unit coupled to the ultrasound transducer and arranged to calculate an image of the part of the body from the ultrasound scan signals provided by the ultrasound transducer;

at least one catheter provided with at least one ultrasound receiver that is coupled to the image processing unit, wherein the image processing unit determines a distance between the at least one transmission unit of the ultrasound transducer and the at least one ultrasound receiver on the at least one catheter from a transit time of the scan signals provided by the ultrasound transducer.

9. An imaging ultrasound system as claimed in claim 8, wherein the ultrasound transducer includes a plurality of transmission units and receiving units arranged to acquire a three-dimensional ultrasound image in conjunction with the image processing unit.

10. An imaging ultrasound system as claimed in claim 8, wherein the catheter is provided with at least three ultrasound receivers.

11. An imaging system as claimed in claim 8, wherein the catheter is provided with electrodes for an acquisition of electrophysiological data.

* * * * *